United States Patent [19]

Silvy et al.

[11] Patent Number: 5,087,823
[45] Date of Patent: Feb. 11, 1992

[54] DEVICE FOR DETERMINING THE CHARACTERISTICS OF PARTICLES IN SUSPENSION IN A LIQUID

[75] Inventors: Jacques Silvy, Grenoble; René Pascal, Meylan, both of France

[73] Assignee: Association de Gestion de l'Ecole Francaise de Papeterie et de l'Imprimerie, Paris, France

[21] Appl. No.: 507,209

[22] Filed: Apr. 11, 1990

[30] Foreign Application Priority Data

Apr. 12, 1989 [FR] France .................. 89 05162

[51] Int. Cl.$^5$ .................. G01N 15/06; D21F 7/06
[52] U.S. Cl. .................. 250/573; 162/263; 356/336; 356/343; 356/338; 250/576; 250/225
[58] Field of Search .................. 162/49, 55, 263; 250/574, 573, 225, 575, 576; 356/336, 338, 343, 335, 337

[56] References Cited

U.S. PATENT DOCUMENTS

| | | | |
|---|---|---|---|
| 3,873,416 | 3/1975 | Forgals et al. | 162/49 |
| 4,276,119 | 6/1981 | Karnis et al. | 162/55 |
| 4,318,180 | 3/1982 | Lundquist et al. | 356/336 |
| 4,692,210 | 9/1987 | Forrester | 162/49 |
| 4,758,308 | 7/1988 | Carr | 162/49 |
| 4,838,692 | 6/1989 | Brenholdt | 250/574 |

FOREIGN PATENT DOCUMENTS

WO88/02855 4/1988 PCT Int'l Appl. .

OTHER PUBLICATIONS

Advances in Instrumentation, vol. 30, Part II, *Continuous Particle Size Analysis and Grinding Control*, 1975.
Tappi, vol. 53, No. 7, *Fractionation of Fiber Suspensions by Liquid Column Flow*, Jul. 1970.

*Primary Examiner*—Davis L. Willis
*Assistant Examiner*—Michael Messinger
*Attorney, Agent, or Firm*—Lowe, Price, LeBlanc and Becker

[57] ABSTRACT

A device for determining the characteristics of particles in suspension in a liquid, comprising a sampling device (2) for injecting samples of particles; a fractionator (3) for sorting those particles as a function of their length; an optical measurement cell (4) which receives the output of the fractionator, and a programmable controller (6) for calculating the values of the intensities and combinations of those values in the various directions of the optical radiation. The optical measurement cell includes a laser for transmitting polarized, coherent light through the particles in suspension and for collecting the light diffracted in various directions.

9 Claims, 3 Drawing Sheets

DEVICE FOR DETERMINING THE CHARACTERISTICS OF PARTICLES IN SUSPENSION IN A LIQUID

BACKGROUND OF THE INVENTION

The present invention relates to a device for determining the characteristics of particles in suspension in a liquid. The invention more particularly applies to determine the characteristics of paper paste constituents during paper manufacturing. It especially permits measurement of parameters such as length, width, curvature and ratio between organic elements and mineral elements.

Suspensions such as paper pastes comprise fibrous organic elements and mineral elements having very diversified shapes, sizes and ratios that have to be known because the properties of the finished product largely depend upon those parameters. Particles comprise fibers, the largest size of which ranges from a few tenths of a millimeter to over one centimeter, which are in suspension in a liquid, usually water.

In the prior art, numerous processes for determining the characteristics of particles in suspension, such as fibers and mineral fillers contained in a paper paste, are known.

Apparatuses have been proposed wherein particles in suspension in a liquid are forced to pass through a transparent cell which is lighted, for example, by a coherent light source, allowing the various following steps to be carried out:

measuring the fiber length by forming the fiber pattern on photodetector lines and counting the number of exposed photodetectors, measuring a size corresponding to their diameter by analyzing the diffraction and diffusion patterns, and measuring the ratio between cellulose fibers and mineral fillers by measuring the depolarization of a light source direct flow.

In case of length measurement, the drawback of this type of apparatus is that it requires the use of an optical measurement cell formed by a small-diameter capillary tube so as to strictly limit the number of fibers that flows therethrough at a given time in order to be able to form individual fiber patterns and to measure the length of the fibers. Indeed, if a large number of fibers simultaneously arrives, their patterns cannot be separated and length cannot be measured. The drawback inherent in the use of a small-diameter capillary tube is that, in addition to an increase in measurement time, in practice such a capillary tube is liable to be clogged by accumulation of particles or by a larger particle. As a result, the above processes using optic measurement cells are not used for industrial manufacturing purposes but only in laboratories by sampling and individually examining those samples.

Independently of the apparatuses for measuring morphologic parameters of fibers or other elements in suspension in a liquid, particle fractionation apparatuses have been used in the paper industry, for sorting paper paste constituents as a function of the fiber length. An exemplary apparatus is described in an article by Gunnar OLGARD issued in TAPPI, Vol. 53, No. 7, July 1970, pages 1240–1270.

Such a fractionation apparatus, or fractionator, comprises a tube through which flows a liquid (eluant) between two air bubbles and in which the particles already in suspension are injected. Particles are then concentrated in suspension and sorted. In paper industry, eluant is generally water. By sending the output product of such a hydrodynamic fractionator into different vessels, for example positioned on a turntable, each of the vessels is filled with eluant containing fibers according to a given range of lengths.

A fractionator is not a measurement apparatus but a sorting device.

An object of the invention is to provide for an apparatus measuring the quantity of particles fractionated by range of size as well as characteristic parameters of fibers or other components in suspension in a liquid, this apparatus having the advantage of being usable for industrial purpose and to permit a periodical follow-up, substantially in real time, of a paper paste in suspension flowing in treatment tubes.

SUMMARY OF THE INVENTION

The invention is based on the observation that, among the parameters liable to be measured by passing through an optical measurement cell, which implies use of a small-size capillary tube, it is only measuring certain parameters that requires individually analyzing a fiber (e.g., measurement of the fiber length), whereas for other parameters the general characteristics of the diffused, diffracted and/or depolarized light is analyzed and statistical results, which do not require any analysis on individual fibers or any other individual element, are obtained.

Thus, the invention provides for associating in a single apparatus a hydrodynamic fractionator and an optical measurement cell directly receiving the output of the fractionator. The latter is used for supplying by range of size, in a diluted and sorted form, the fiber samples that are introduced therein. The arrival moments of the fibers into the measurement cell with respect to the injection moment into the fractionator give, in relation with a calibration, a measure of the fiber length, whereas the quantity of those fibers as well as the other parameters associated therewith are detected by optical detectors and other treatment devices associated with the optical measurement cell.

It is then possible to analyze a large number of fibers simultaneously flowing and it is no longer necessary to provide a very small-size capillary tube for the optical measurement cell. The measurement apparatus according to the invention therefore operates at a high flow rate without clogging.

More specifically, the invention provides for a device for determining the characteristics of the particles in suspension in a liquid, comprising means for injecting particle samples; a fractionator which classifies those particles as a function of a first parameter and supplies them at its output in a time sequenced and determined mode as a function of this first parameter; an optical measurement cell receiving the output of the fractionator, this optical measurement cell comprising means for sending a polarized coherent electromagnetic radiation through the flow of particles in suspension and for collecting the diffracted and possibly depolarized light, partially absorbed and diffused in various directions; and means for calculating the values of intensities and combinations of those values in the various directions of the optical radiation.

According to an embodiment of the invention, the fractionator is a hydrodynamic fractionator diluting the suspension and carrying out a classification giving priority to the particle length, this element being constituted by a tube, the cross section of which is low with respect to its length, determined quantities of samples of particles in suspension in a liquid being injected at determined times into the tube in which flows an eluant at a controlled flow rate.

According to an embodiment of the invention, at the output of the optical measurment cell is provided a turntable, the operation of which is synchronized with the injection periods of samples of particles in suspension for collecting successive fractions of the fluid containing particles sorted according to the first parameter.

According to an embodiment of the invention, a programmable controller ensures sequencing between the injection of the samples into the fractionator and the measurements by the detectors associated with the optical measurement cell for especially measuring at each moment corresponding to particles with a determined length, their quantity, width, curvature and the ratio between the mineral and organic elements.

According to an embodiment of the invention, the light collecting means comprises photodetectors arranged in a circle to permit an angular analysis of the diffracted light intensity and calculation means for deducing a shape factor of the particles in the measurement cell.

The particles being diluted and sorted as a function of their length by passing through the hydrodynamic fractionator, the output product of the device according to the invention is also sorted as a function of the particle length. The output product can then be routed towards different outputs during successive time periods, for allowing complementary measurements to be carried out on the sorted particles.

BRIEF DISCLOSURE OF THE DRAWINGS

The foregoing and other objects, features and advantages of the invention will be apparent from the following detailed description of preferred embodiments as illustrated in the accompanying drawings wherein.

GENERAL STRUCTURE OF THE INVENTION

Figure 1:
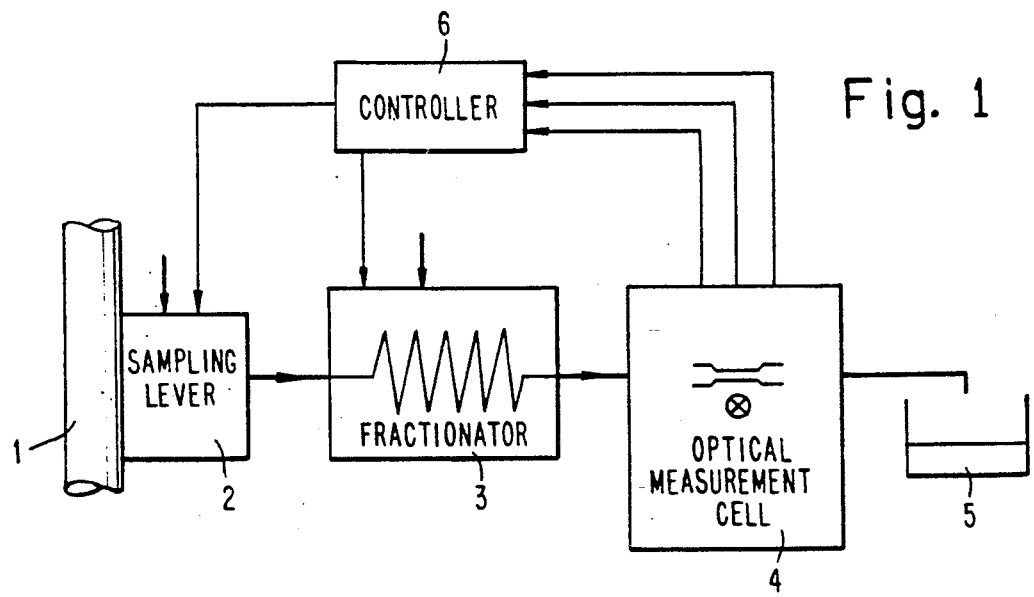
FIG. 1 is a partial block diagram of the general arrangement of a device according to the invention.

FIG. 1 schematically shows block diagrams of the general arrangement of a device for measuring the characteristics of elements diluted in water, such as fibers and mineral fillers, flowing in a pipe 1 of a paper plant. A sampling device 2 permits taking of samples of the paper paste flowing in pipe 1 at determined moments, then injecting them into a fractionator 3 constituted for example by a long pipe permanently fed with fluid. The output product of fractionator 3 is routed towards an optical measurement cell 4 and, after measurement, the fluid is poured into a tank 5 and may possibly be recovered. Synchronization of the system is ensured by a programmable controller 6 which sends appropriate signals to the various valves and draws at determined moments the output products of the detectors associated with the measurement means 4. This programmable controller may incorporate a microprocessor. The fractionator 3 sends to the measurement cell particles having sequentially decreasing lengths and optical measurement cell 4 measures the quantity of fibers during the various sequences as well as parameters of the fibers and mineral fillers other than length.

SAMPLING DEVICE

Figure 2:
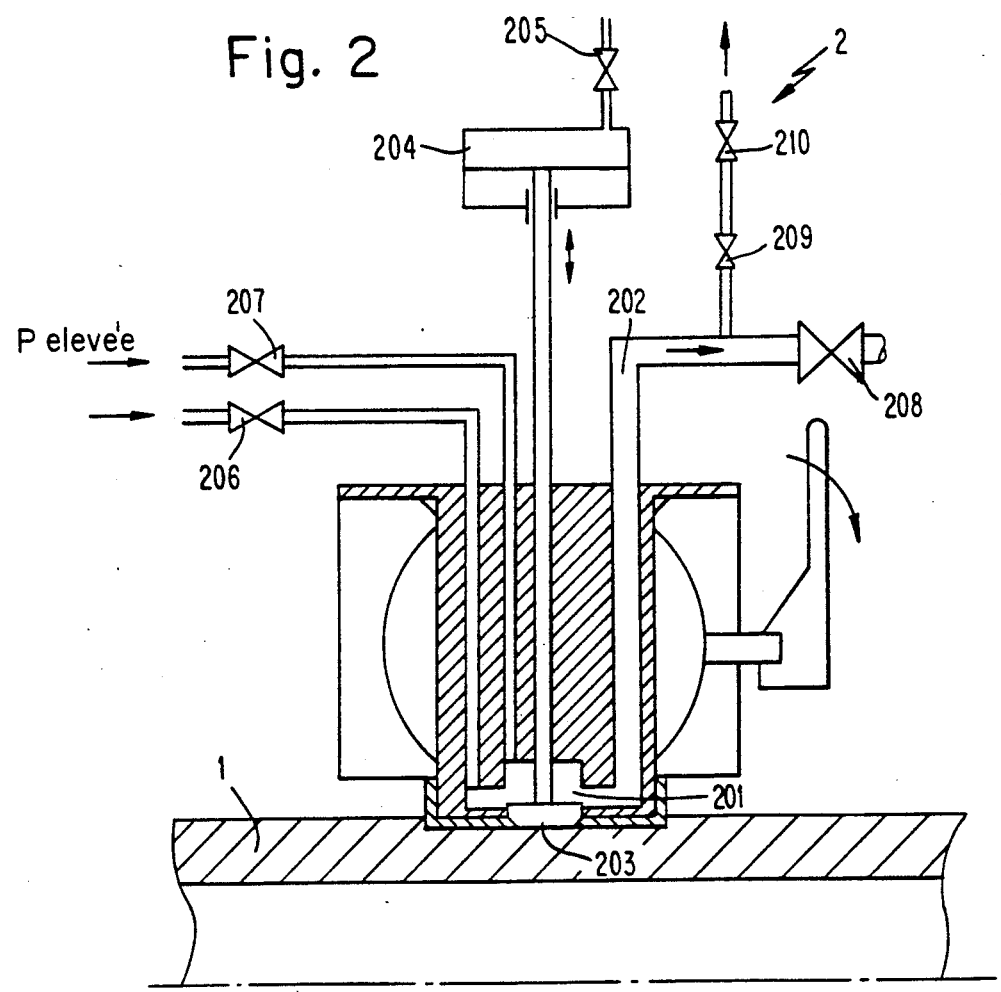
FIG. 2 is an exemplary automatic sampling device on a paper paste pipe.

FIG. 2 illustrates an exemplary embodiment of the sampling device 2. The latter comprises a chamber 201 extended by a pipe portion 202. Chamber 201 communicates with pipe 1 through a valve 203 controlled by an actuator 204 operated by a manifold distributor 205, in turn controlled by the programmable controller 6. Water intakes to chamber 201 and pipe 202 are controlled by valves 206 and 207, valve 206 receiving water under a normal pressure and valve 207 receiving water under high pressure, and more particularly at a pressure high than that in pipe 1. The pipe portion 202 communicates by a valve 208 with the input of the fractionator 3. A valve 209 and a flow limiter 210 permit evacuation of the portion of pipe 202. All the above cited valves operate under the control of the programmable controller 6.

A sampling operation follows the steps indicated in table I, wherein letter C designates a closing phase of the valve and letter O and opening phase.

TABLE I

|         | 207 | 206 | 208 | 203 | 209 |
|---------|-----|-----|-----|-----|-----|
| Phase 1 | C   | O   | O   | C   | C   |
| Phase 2 | C   | C   | C   | C   | C   |
| Phase 3 | C   | C   | C   | O   | O   |
| Phase 4 | O   | C   | C   | C   | C   |
| Phase 1 | C   | O   | O   | C   | C   |

The succession of sampling phases is as follows.

Phase 1

Valves 206 and 208 are open, the other valves being closed. Water flows through chamber 201 and pipe 202 to flow out towards the fractionator 3. This is the phase having the longest time duration during which a sample, previously sampled, flows in the fractionator.

Phase 2

During a very short period of time, all the valves are closed.

Phase 3

Pure water intake valves 206 and 207 and output valve 208 are closed, valve 203 is open as well as valve 209. Chamber 201 and the pipe portion 202 are filled with paste in suspension coming from pipe 1 at a constant rate determined by limiter 210 to admit a given volume of paper paste as a function of the opening time period of the valves.

Phase 4

Although specific states are indicated in table I for this phase, it is a transitory phase during which valve 203 is being closed by the effect of actuator 204. During this phase, valve 207 is open to allow pure water to be injected under high pressure, higher than the paper paste pressure in pipe 1 in order to rinse the seat of valve 203 and to avoid leakages due to the presence of chocked fibers at the closing period.

Then, phase 1 is started again and the drawn sample contained in chamber 201 and pipe 202 flows out into the fractionator.

The aim of the description and illustration in FIG. 2 of the sampling device is only to show it is possible, in industrial use, to automatically draw samples having a determined volume from the pipe of paper paste 1 and to inject same into a fractionator 3. Any other means for injecting given volumes of paper paste samples at the input of the fractionator can be devised by those skilled in the art without departing from the scope of the invention.

The fractionator 3 can for example be constituted by a semi-rigid plastic material pipe having a section of a few tens to a few hundreds mm$^2$ and a length of about a few tens to a few hundreds meters, this pipe being for example rolled up to reduce bulkiness.

MEASUREMENT CELL

Figure 3:
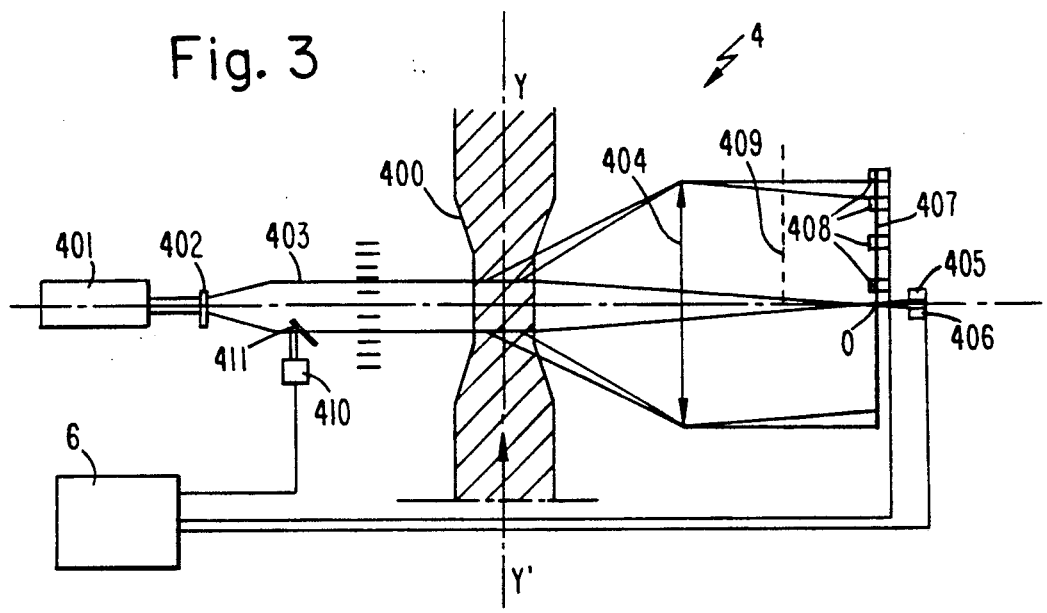
FIG. 3 is a schematic drawing of the measurement cell and of the associated devices.

FIG. 3 schematically shows an embodiment of the optical measurement cell 4.

The fluid flowing out from the fractionator 3 flows in a measurement cell 400 constituted by a pipe portion having a small section and parallel plane surfaces made of a material transparent to a polarized electromagnetic radiation, preferably associated to an input convergent funnel and an output divergent funnel. The radiation source is for example a polarized helium-neon laser 401, the beam of which is expanded by an optical system 402 for supplying a parallel ray beam 403, having for example a diameter of several millimeters, which is sent into the small section portion 400.

The beam is collected by a lens 404 and, in the absence of particles, is focussed at point 0 of a measurement plane 407. Phototransistors or other photodetectors 405 and 406 are placed on both sides of point 0 and at its neighbourhood. One of the phototransistors, for example phototransistor 405, is preceded by a polarizer 409 ensuring cutoff of the incoming beam in the absence of depolarization. Polarizer 409, the polarization direction of which is orthogonal with respect to the polarization plane of the incoming beam, arranged according to an angle of 45° with respect to the main axis (YY') of the fiber direction in the cell, is positioned on one half of the analysis plane which is then separated into two circular semi-sectors delineated by diameter YY' as shown in FIG. 4.

When particles flow in the measurement cell 400, the beam is diffracted, diffused and possibly depolarized. Its intensity in various directions is detected in measurement plane 407 by photodetectors 405 and 406 and by photodetectors 408 placed apart from the center.

Figure 4:
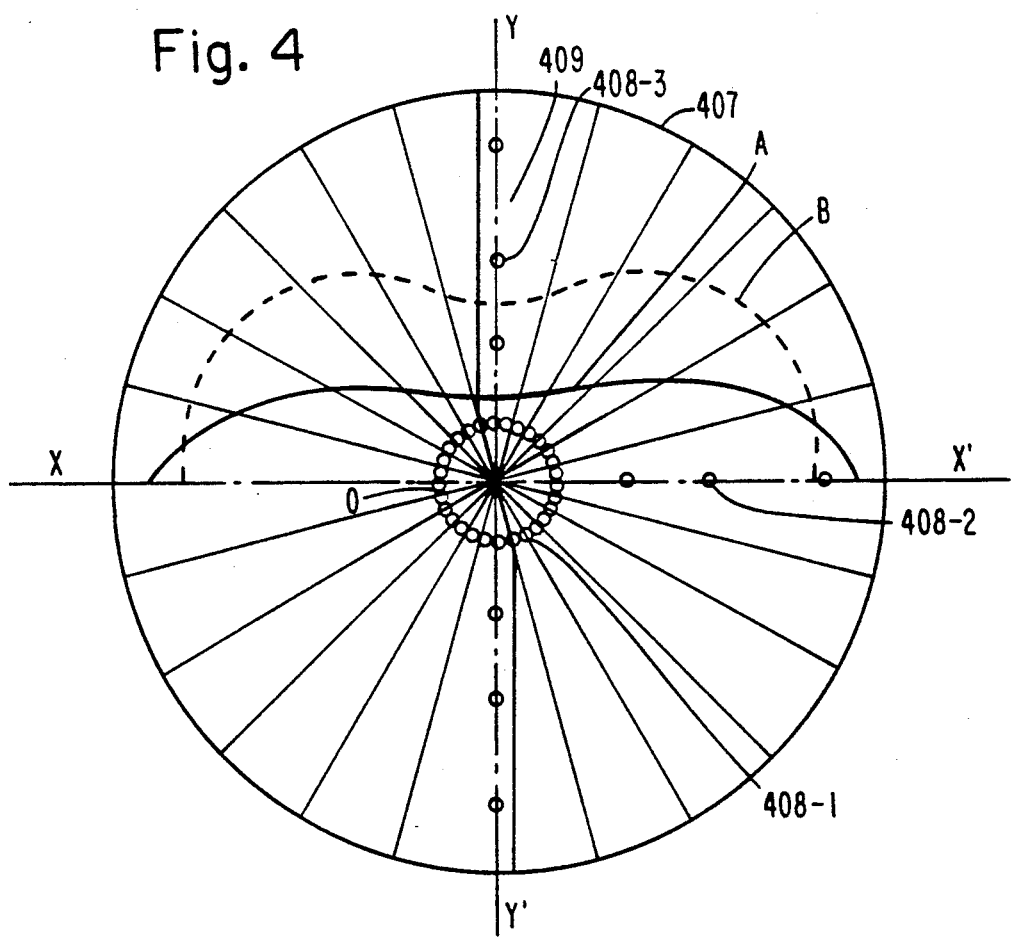
FIG. 4 represents an exemplary arrangement of the photosensitive elements in the plane of the diffraction pattern.

FIG. 4 represents a front view of measurement plane 407 and the arrangement of photodetectors 408 in this plane. Before describing this figure in more detail, it will also be noted in FIG. 3 that the various photodetectors 405, 406, 408, as well as an additional detector 410, receiving a portion of the incoming beam drawn for example by a semi-transparent mirror 411 are connected to the programmable controller 6 for being processed. The controller will use in particular the signal of detector 410 as a reference for the intensity of laser beam 401. Moreover, a signal variation on the signals of photodetectors 405 and 406 will permit to indicate when the fibers start passing into the measurement cell. A calibration of the device will permit determination, as a function of the volume of eluant which has flowed, the length of the first incoming fibers, then to know at any time the length of the fibers crossing the measurement cell, this calibration depending upon the volume drawn by sampling device 2, the characteristics of fractionator 3 and the composition of the sample.

The operation of the measurement system will now be described in more detail by considering the arrangement of detectors 408 in the measurement plane 407. In this figure, photodetectors are represented by small circles. A first set of detectors 408-1 is distributed over a circle centered on the focus; a second set of detectors 408-2 is positioned on the semi-diameter OX'; and a third set of detectors 408-3 is positioned according to diameter YY'. Polarizer 409 extends over half of the measurement plane and is indicated by a boundary drawn in solid thick lines, substantially corresponding to axis YY' but extending beyond detectors 408-3 in the upper portion of the figure and below, inside the lower portion of the figure.

This arrangement of the detectors permits analysis of the diffraction pattern and the polarization state of the beam which has crossed the measurement cell.

The upper half plane of FIG. 4 shows the distribution of the intensity received in the measurement plane 407 in two specific cases. Curve A represents the distribution of the diffracted intensity for a set of fiber elements relatively rectilinear preferably directed according to axis YY', that is, the measurement cell axis. Curve B represents the distribution of the intensity for the fiber elements, the curvature of which is more accentuated but the general direction of which is still YY'. Comparison of signals from detectors 408-1 provides an information characterizing the fiber curvature.

In practice, some types of elements passing through the measurement cell cause a light depolarization (for example in case of cellulose fibers). Then, as shown, curves A and B, symmetrical with respect to axis OY (within the attenuation factor of polarizer 409) are obtained. Other particles will not depolarize light. The intensity received behind polarizer 409 will then be very low. Then, curves asymmetrical with respect to OY are obtained. Thus, the signals supplied by photodetectors 408 will supply, in addition to an information on the curvature, information on the nature of the elements passing in the measurement cell.

Figure 5:
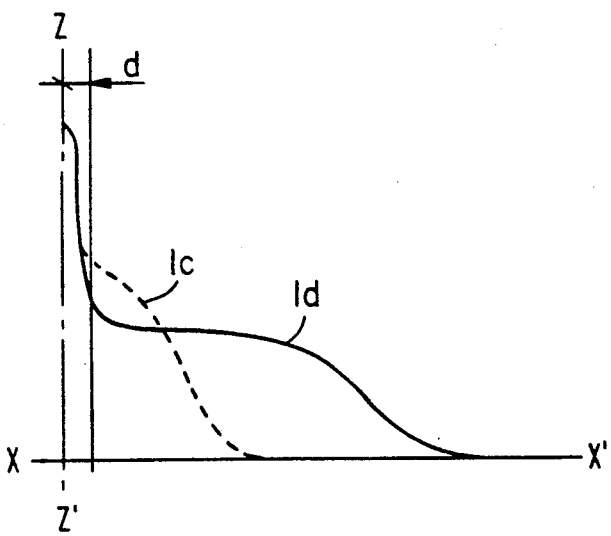
FIG. 5 shows the shape of the light intensity variations measured by the photosensitive detectors permitting to determine the characteristics of particles having various diameters.

FIG. 5 exemplarily illustrates the distribution of the diffracted radiation intensity according to direction XX' by particles having different diameters and determined length. This measurement is carried out by detectors 408-2 positioned on axis XX'. Curve $I_c$ represents the diffracted energy distribution for particles having relatively large diameter, and curve $I_d$ the energy distribution for particles having small diameter. It can be seen that, in both cases, the intensity is relatively high at the neighbourhood of the center, in the area labelled d, then the intensity more or less slowly decreases before dropping. This decrease is all the more accentuated that the diameter of the particle is higher. Thus, the intensity distribution according to axis XX' gives an indication on the diameter of the fibers flowing in the cell.

Detectors 408-3 arranged on axis YY' are more particularly designed to determine the characteristics of the particles having a more or less isometric shape and small size. It is reminded that polarizer 409, crossed with respect to the polarization direction of the source laser, is positioned in front of detectors 408-3 along the semi-axis OY and not in front of detectors 408-3 arranged along the semi-axis OY'. Therefore, one obtains an intensity distribution characteristic of a possible depolarization, the result of which permits to differentiate the mineral particles from the cellulose fibers.

Although an arrangement and a preferred embodiment of detectors has been above described, those skilled in the art will be able to use the signals of the various detectors for obtaining further information. For example, it will be possible to copy the image on plane 407 in a camera and to analyze its various components in a desired way.

On the other hand, while a measurement cell with parallel faces has been above described, it is possible to adopt a cylindrical cell, that is, a simple portion of glass tube (which is not a capillary tube). In that case, the above disclosure can be altered as necessary, with the measurement plane being a cylindrical measurement surface.

MEASUREMENT CYCLE

The overall arrangement of the measurement device according to the invention and prefered embodiments of some of its constituents being described, a measurement sequence will now be disclosed, being clear that such a sequence will periodically be repeated. Those measurement sequences are set by the programmable controller 6.

Figure 6:
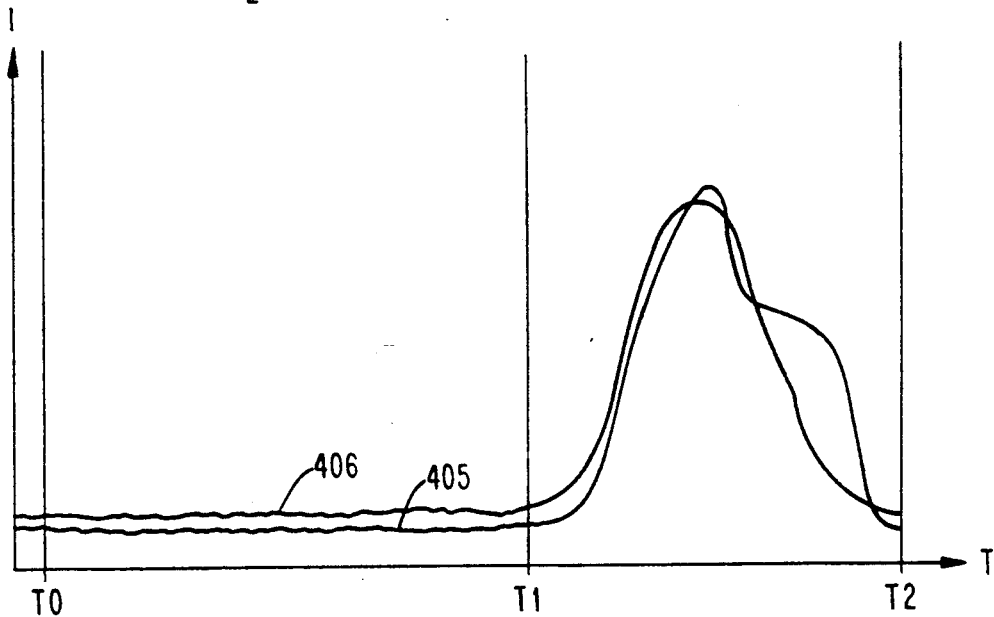
FIG. 6 represents a light intensity curve as a function of time at the neighbourhood of the optical axis of the measurement system.

Considering table I at a time To at the beginning of phase 1, immediately after phase 4 during which is injected a sample, pure eluant flows through the optical measurement cell. From that time, as indicated in FIG. 6, detectors 405, 406 and 408 only supply noise signals. From a time T1, the detectors start supplying more accentuated signals, which indicates that the first fibers (the longest ones) are arriving in the measurement cell. FIG. 6 shows an exemplary variation of intensity received by detectors 405 and 406 within the time interval T1-T2 during which the sample passes through the measurement cell. As seen above, detector 406 receives light from source 401 after crossing the whole system but without passing through a polarization analyzer. Detector 405 receives the light that has crossed the polarization analyzer 409. Thus, the first function of detectors 405 and 406 is to indicate the quantity of fibers having different lengths flowing in the measurement cell at any time.

Figure 7:
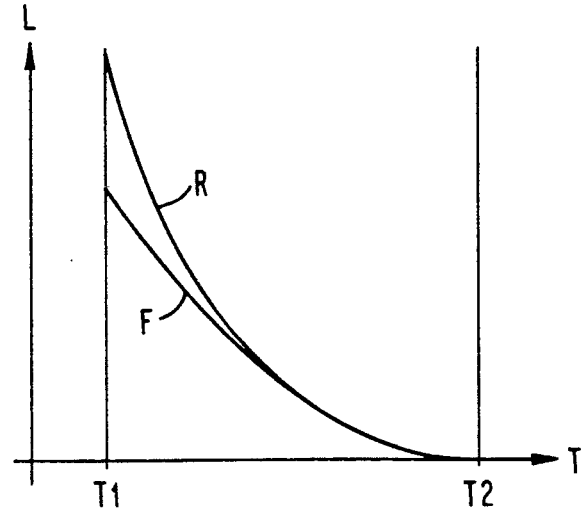
FIG. 7 represents a calibration curve of the fiber lengths as a function of time for a device according to the invention.

For determined eluant volumes flowing with a flow rate carefully kept constant, it is possible, as indicated in FIG. 7, to calibrate the system to have each time period in the time interval T1-T2 correspond to a length L of the fibers passing in the measurement cell. In FIG. 7, the curve R corresponds to a calibration of resinous fibers and curve F to a calibration of foliaceous fibers.

The information on the times T1 and T2 being received by the programmable controller 6, the latter consequently triggers the collecting of information from the various detectors 405, 406, 408-1, 408-2 and 408-3 above described in relation with FIG. 4. The programmable controller is also liable to choose to carry out measurements during the time interval T0-T1, when, normally, only pure eluant flows, for detecting the noise levels that will be substracted from the measurement levels of the various detectors.

Moreover, the programmable controller will be able to control reinjection of samples at determined times, spaced by a time duration higher than the time interval T1-T2 so that samples do not overlap in the fractionator 3. In addition, as above indicated, the output flow from the measurement cell may be routed towards tanks fixed on a turntable. Thus, one obtains a means for sorting particles according to length classification, which also permits subsequently checking the optical measurements previously carried out, or any other measurement.

More particularly, the aim of the invention is to determine morphologic characteristics of paper pastes during the manufacturing steps on the production lines of papers, cardboards and similar materials essentially formed by fibrous particles. Measurement of the fiber length can be used, for example, for adjusting paper paste refiners and calculating the ratio between organic and mineral elements for setting the fiber composition as well as the retention control of the mineral fillers in the paper manufacturing process. The invention is also usable in laboratories and for determining the morphology of any type of particle, either mono or polydispersed in suspension in a liquid. An application of the invention consist in combining the above system with the display of particles flowing in the suspension before and/or after their classification, thus permitting to compare quantitative information collected in the above described process with the specific and subjective characteristics of the particles when they are observed moving in the flowing suspension shown by the pattern. The described device facilitates measurements owing to the analysis of sample patterns previously drawn and classified, to be quantitatively measured by appropriate softwares.

On the other hand, while specific sampler, fractionator and measurement cell have been described, those skilled in the art will be able to choose other equivalent, simpler or more complex devices.

We claim:

1. A device for determining the characteristics of particles in suspension in a liquid as a function of a size parameter of said particles, comprising:
    means for collecting samples of said particles,
    a fractionator which classifies said particles in each of said samples into a continuous sequence ordered according to said size parameter,
    an optical measurement cell which receives said continuous sequence from said fractionator, said cell comprising means for sending a polarized coherent optical radiation through the flow of particles in suspension and for collecting diffracted, possibly depolarized light, partially absorbed and diffused in various directions, and
    means for calculating the values of the intensities and combinations of said values in the various directions of said optical radiation.

2. A device for determining the characteristics of particles in suspension in a liquid according to claim 1, wherein said fractionator is a hydrodynamic sorting device, sorting in priority said particles as a function of their length, said fractionator comprising a tube, the cross-section of which is small relative to its length, wherein each of said samples is injected at a specified time into said tube and wherein an eluant flows in said tube at a specified rate.

3. A device for determining the characteristics of particles in suspension in a liquid according to claim 2, further comprising at the output of said optical measurement cell a turntable, the operation of which is synchronized with said specified time at which each said sample is injected.

4. A device for determining the characteristics of particles in suspension in a liquid according to claim 1, wherein said collecting means comprises means for automatically drawing at specified times said samples from a liquid containing said particles in suspension from a tube of an industrial line, and injecting said samples into said fractionator.

5. A device for determining the characteristics of particles in suspension in a liquid according to claim 2, further comprising a programmable controller for sequencing injection of said samples into said fractionator and a plurality of detectors associated with said optical measurement cell for measuring at each moment corresponding to said particles of a given length, their quantity, width, curvature and ratio between the mineral and organic elements therein.

6. A device for determining the characteristics of particles in suspension in a liquid according to claim 1, wherein said measurement cell is a transparent tube with a cylindrical section.

7. A device for determining the characteristics of particles in suspension in a liquid according to claim 2, wherein said means for collecting light comprises photodetectors arranged in a circle for allowing said diffracted light to be sectorially analyzed and wherein said calculating means comprises means for deducing a shape factor of said particles in said measurement cell.

8. A device for determining the characteristics of particles in suspension in a liquid according to claim 1, wherein said optical radiation sent into said measurement cell is polarized at an angle of 45° with respect to the direction of the preferential axis of those of said particles longitudinally positioned in the measurement cell, and wherein a portion of said detectors are preceded by a cross-polarization analyser.

9. A device for determining the characteristics of particles in suspension in a liquid according to claim 8, comprising means for comparing the signals of the detectors symetrically arranged with respect to said preferential axis in the diffracted light region, some of said detectors being placed behind said analyzer, and others not.

* * * * *